United States Patent [19]

McKaba et al.

[11] Patent Number: 4,530,830
[45] Date of Patent: Jul. 23, 1985

[54] QUATERNARY AMMONIUM HYDROXIDE HAIR RELAXER COMPOSITION

[75] Inventors: William McKaba; Clyde B. Simpson, both of Jacksonville, Fla.

[73] Assignee: Revlon, Inc., New York, N.Y.

[21] Appl. No.: 562,268

[22] Filed: Dec. 16, 1983

Related U.S. Application Data

[63] Continuation-in-part of Ser. No. 374,841, May 2, 1982, abandoned.

[51] Int. Cl.³ .................. A61K 7/09; A61K 7/11; A61K 7/06
[52] U.S. Cl. ........................................ 424/71; 424/70
[58] Field of Search ...................... 424/70, 71, 329

[56] References Cited

U.S. PATENT DOCUMENTS

| | | | |
|---|---|---|---|
| 3,017,328 | 1/1962 | Childrey et al. | 424/71 |
| 4,010,872 | 3/1977 | Lozano et al. | 424/73 |
| 4,119,399 | 10/1978 | Feinland et al. | 424/70 |
| 4,402,700 | 9/1983 | Feinland et al. | 424/70 |

OTHER PUBLICATIONS

*Clinical Toxicology of Commercial Products,* "Quat. Amm. Cmpds.", pp. 197–200, (1971).
*Merck Index,* 9th ed., Abst. 8919 and 8939.

*Primary Examiner*—Albert T. Meyers
*Assistant Examiner*—F. Abramson

[57] ABSTRACT

Provided is a novel composition for use in hair relaxing. The composition contains a quaternary ammonium hydroxide and a cosmetic base.

12 Claims, No Drawings

QUATERNARY AMMONIUM HYDROXIDE HAIR RELAXER COMPOSITION

This application is a continuation-in-part of application Ser. No. 374,841, filed May 2, 1982, abandoned.

BACKGROUND OF THE INVENTION (1) Field of the Invention

This invention relates to hair relaxing compositions for straightening of the hair and, more specifically, relates to improved compositions containing a quaternary ammonium hydroxide.

(2) Prior Art

It is known that the configuration of hair can be altered from curled to straight, for example, by subjecting the hair to the action of a composition which relaxes the hair by rupturing the disulfide bonds in the keratin of the hair to produce free sulfhydryl groups followed by setting with an oxidizing agent. The use of high alkalinity chemicals is also an effective way of modifying the configuration of the hair.

The compositions most commonly used as relaxers are based on sodium hydroxide, sulfite, or thioglycolate. When these products are used to relax the hair, the sulfite and thioglycolate-based products are less effective than sodium hydroxide; thus in the United States the hydroxide is the preferred product for straightening in the salon.

The prior art in an effort to minimize irritation decreased the amount of sodium hydroxide present in hair relaxer compositions. However, compositions having sodium hydroxide in amounts of 3 to 4% are still irritating and further reduction of the concentration in certain oily carriers can result in an ineffective, unpractical product. To further minimize the problems associated with the use of sodium hydroxide containing products the prior art provided for pre-treatment of the hair prior to application of the hair relaxer. In the pre-treatment procedure an oily mixture is deposited on the hair and scalp to form a coating thereon to at least partially shield hair keratin and scalp from the reductive action of the sodium hydroxide.

While the sodium hydroxide and thioglycolate products are irritants and can damage hair, the sulfite products are not effective enough to be permanent relaxers.

A recent development is the use of guanidine hydroxide as a relaxer. However, this product is not stable and must be supplied in two parts; one containing calcium hydroxide and the other quanidine carbonate. The consumer must mix the two parts together prior to being used.

Accordingly, it is an object of the present invention to provide a hair straightening composition that is not as irritating as the sodium hydroxide products.

It is another object of the present invention to provide a composition which does not require mixing to form the active ingredient just prior to its application to the hair.

It is still another object of the present invention to provide a stable formulation in a stable cream base.

It is a further object of the present invention to provide a method for straightening hair in an effective and convenient manner without deleterious effect on the hair and scalp of the user.

SUMMARY OF THE INVENTION

It has now been discovered that the configuration of the hair can be effectively changed by the application of a composition comprising a quaternary ammonium hydroxide in a stable aqueous, cosmetic base.

While it is within the spirit of the invention to utilize a quaternary ammonium hydroxide which has merely been diluted in water to a strength which will be effective while not being excessively irritating to the scalp, the scope of the invention is contemplated to cover quaternary ammonium hydroxides in an emulsion which is not only more readily utilized by the beauty operator or consumer but also inhibits the irritating tendency exhibited by some of the quaternary ammonium hydroxides at a higher, more effective level of concentrations.

The hair straightening or relaxing composition of the present invention utilizes a quaternary ammonium hydroxide being present by weight based on the weight of the total composition in about 2 to 20%, more preferably about 2.5 to 10%, and most preferably about 2.5 to 8%. Preferred quaternary ammonium hydroxides include methyl triethanol ammonium hydroxide and tetraethyl ammonium hydroxide. Some of the other quaternary ammonium hydroxides suitable for use as hair relaxers include:

benzyltrimethyl ammonium hydroxide
tetramethyl ammonium hydroxide
tetrabutyl ammonium hydroxide
tetrapropyl ammonium hydroxide
methyl triethanol ammonium hydroxide
benzyl dimethyl ethanol ammonium hydroxide
benzyltriethyl ammonium hydroxide
benzyltributyl ammonium hydroxide
octadecyl trimethyl ammonium hydroxide
tetra hexyl ammonium hydroxide and
tetra octyl ammonium hydroxide.

The quaternary ammonium hydroxide is formulated into an aqueous cosmetic emulsion, such as a creme or lotion, which comprises as essential ingredients an emulsifier and an emollient. Based on the total weight of the formulation the emulsifier is present in an amount of 2 to 20%, preferably 10–15%; while the emollient is present in an amount of 2 to 30% and preferably 5 to 25%. The remaining amounts of the composition comprises water.

Emulsifying agents as used herein denote agents that provide for dispersion of the ingredients, insure suspension thereof, and render a creamy and lubricous consistency to the composition.

The emulsifying agents suitable for the purposes of the present invention may be characterized as nonionic agents which, by themselves or by interacting with other ingredients present in the formulation, do not cause irritation to the skin. It was found that anionic emulsifying agents, such as sodium lauryl sulfate, are not desirable in hair relaxing compositions because of their tendency to heighten irritation in combination with the active hair relaxers. Suitable emulsifiers include:

Polyethylene glycol ether of cetyl alcohol (that conforms to the formula $CH_3(CH_2)_{14}CH_2(OCH_2CH_2)_nOH$, wherein n has an average value of 20, sold under the tradename Ceteth-20);

Polyethylene glycol ether of lauryl alcohol (having the formula $CH_3(CH_2)_{10}CH_2(OCH_2CH_2)_nOH$, wherein n has an average value of 23, sold under the tradename Laureth-23);

Polyethylene glycol ether of nonyl phenol (sold under the tradename Nonoxynol-10); and Polyethylene glycol ether of lanolin alcohol.

The emollient used in the formulations of the present invention include:

Cetyl alcohol (fatty alcohol having the formula $CH_3(CH_2)_{14}CH_2OH$)

Petrolatum (a semi solid mixture of hydrocarbons obtained from petroleum);

Stearyl alcohol (fatty alcohol having the formula $CH_3(CH_2)_{16}CH_2OH$);

Paraffin (solid mixture of hydrocarbons obtained from petroleum characterized by large crystals); and Mineral oil (liquid mixture of hydrocarbons obtained from petroleum);

Lanolin alcohol (mixture of organic alcohols obtained by the hydrolysis of lanolin);

Polyethylene glycol ether of octyl phenol (N=1 or 3).

The composition obtionally contains a fragrance, usually under 1%, chelating agents usually under 1%, and humectins, 0–20%, preferably 4–15%. Chelating agents include polyphosphates and ethylene diamine tetraacetic acid (EDTA). Humectins include propylene glycol, glycerin, sorbitol and hexylene glycol.

DETAILED DESCRIPTION OF THE INVENTION

The hair relaxing composition of the present invention relaxes the hair by rupturing the disulfide bonds in the keratin of the hair to produce free sulfhydryl groups. This breakage in the disulfide diminishes the rigidity of the hair proteins, leaving the hair pliable and soft.

Heretofore, quaternary ammonium hydroxides have been used in hair dye compositions and in conjunction with oxidizing agents. It has now been discovered that quaternary ammonium hydroxides can be used for hair relaxing prurposes in a suitable carrier, such as a creme or lotion. Such compositions of the present invention are capable of relaxing hair without the degree of irritation characteristic of inorganic hair relaxers, mainly sodium hydroxide based hair relaxers.

The amount of quaternary ammonium hydroxide present should be an amount sufficient to relax the hair without being too much to cause severe irritation.

The amount of quaternary ammonium hydroxide utilized will depend on the specific compound used and on the amount of hair relaxing desired. For example, when the compound is tetraethyl ammonium hydroxide; for mild relaxing, 3.0–4.0% will be used, for medium relaxing, 4.0–5.0% and for regular, 5.0–7.0%.

The compositions of the present invention can be made by art-recognized methods using commercially available ingredients.

The following compositions are representative of the invention. All percentages are by weight. Following the examples described are manufacturing procedures for making the compositions of the examples.

EXAMPLE 1

| | % |
|---|---|
| Water | 53.45 |
| Propylene Glycol | 5.00 |
| Cetyl Alcohol | 9.00 |
| Paraffin | 5.00 |
| Petrolatum | 5.00 |

-continued

| | % |
|---|---|
| Ceteth-20 | 6.00 |
| Octoxynol-1 | 6.00 |
| EDTA | 0.05 |
| Tetraethyl Ammonium Hydroxide (40% aqueous solution) | 10.00 |
| Fragrance | 0.50 |
| | 100.00% |

Manufacturing procedure:

Step 1. Heat the cetyl alcohol, paraffin, petrolatum, Ceteth-20 and Octoxynol-1 to 180° F.

Step 2. Heat water and propylene glycol mixture to 180° F.

Step 3. Add the water and propylene glycol mixture to the mixture of Step 1.

Step 4. Stir to 150° F., add the tetraethyl ammonium hydroxide and EDTA and fragrance. Stir down to 75° F. to finish. Fill into jars of desired size.

EXAMPLE 2

| | % |
|---|---|
| Water | 57.45 |
| Propylene Glycol | 5.00 |
| Cetyl Alcohol | 9.00 |
| Stearyl Alcohol | 5.00 |
| Lanolin | 5.00 |
| Ceteth-20 | 6.00 |
| EDTA | 0.05 |
| Benzyltrimethyl Ammonium Hydroxide 40% | 12.00 |
| Fragrance | 0.05 |
| | 100.00% |

Appearance: off-white, soft cream

Manufacturing procedure:

Step 1. Heat the cetyl alcohol, stearyl alcohol, lanolin and Ceteth-20 to 180° F.

Step 2. Heat water and propylene glycol mixture to 180° F.

Step 3. Add the mixture and propylene glycol mixture to the mixture of Step 1.

Step 4. Stir down to 150° F., add the benzyltrimethyl ammonium hydroxide, EDTA and Fragrance. Stir down to 75° F. to finish. Fill into jars of desired size.

EXAMPLE 3

| | % |
|---|---|
| Water | 53.45 |
| Propylene Glycol | 5.00 |
| Stearyl Alcohol | 9.00 |
| Petrolatum | 5.00 |
| Mineral Oil | 10.00 |
| Laneth-15 | 5.00 |
| EDTA | 0.05 |
| Tetra Octyl Ammonium Hydroxide 40% | 12.00 |
| Fragrance | 0.50 |
| | 100.00% |

Manufacturing procedure:

Step 1. Heat stearyl alcohol, mineral oil, petrolatum and Laneth-15 to 180° F.

Step 2. Heat water and propylene glycol mixture to 180° F.

Step 3. Add the water and propylene glycol mixture to the mixture of Step 1.

Step 4. Stir down to 150° F., add the tetra octyl ammonium hydroxide, EDTA and fragrance. Stir down to 75° F. to finish. Fill into jars of desired size.

EXAMPLE 4

|  | % |
|---|---|
| Water | 55.45 |
| Propylene Glycol | 5.00 |
| Cetyl Alcohol | 9.00 |
| Paraffin | 10.00 |
| Octoxynol-1 | 5.00 |
| Laureth-23 | 5.00 |
| EDTA | 0.05 |
| Tetra Ethyl Ammonium Hydroxide 40% | 10.00 |
| Fragrance | 0.50 |
|  | 100.00% |

Manufacturing procedure:

Step 1. Heat cetyl alcohol, paraffin, Octoxynol-1 and Laureth-23 to 180° F.

Step 2. Heat water and propylene glycol mixture to 180° F.

Step 3. Add the water and propylene glycol mixture to the mixture of Step 1.

Step 4. Stir down to 150° F., add the tetra ethyl ammonium hydroxide, EDTA and fragrance. Stir down to 75° F. to finish. Fill into jars of desired size.

Following are further examples illustrative of the invention:

EXAMPLE 5

|  | % |
|---|---|
| Water | 51.45 |
| Propylene Glycol | 5.00 |
| Cetyl Alcohol | 9.00 |
| Paraffin | 5.00 |
| Petrolatum | 5.00 |
| Ceteth-20 | 6.00 |
| Octoxynol-1 | 6.00 |
| EDTA | 0.05 |
| Methyl Triethanol Ammonium Hydroxide (50% aqueous solution) | 12.00 |
| Fragrance | 0.05 |
|  | 100.00% |

Appearance: firm, white creme

EXAMPLE 6

|  | % |
|---|---|
| Water | 57.45 |
| Propylene Glycol | 5.00 |
| Cetyl Alcohol | 9.00 |
| Ozokerite | 5.00 |
| Mineral Oil | 5.00 |
| Ceteth-20 | 6.00 |
| EDTA | 0.05 |
| Tetraethyl Ammonium Hydroxide 40% | 12.00 |
| Fragrance | 0.50 |
|  | 100.00% |

Appearance: firm, white creme

EXAMPLE 7

|  | % |
|---|---|
| Water | 52.45 |
| Propylene Glycol | 5.00 |
| Stearyl Alcohol | 9.00 |
| Paraffin | 5.00 |
| Octoxynol-5 | 6.00 |
| Lanolin | 5.00 |
| Ceteth-20 | 5.00 |
| EDTA | 0.05 |
| Methyl Triethanol Ammonium Hydroxide 50% | 12.00 |
| Fragrance | 0.50 |
|  | 100.00% |

Appearance: off-white smooth lotion

EXAMPLE 8

|  | % |
|---|---|
| Water | 57.45 |
| Propylene Glycol | 5.00 |
| Stearyl Alcohol | 9.00 |
| Mineral Oil | 5.00 |
| Ceteth-20 | 5.00 |
| Laneth-15 | 6.00 |
| EDTA | 0.05 |
| Benzyltrimethyl Ammonium Hydroxide 40% | 12.00 |
| Fragrance | 0.50 |
|  | 100.00% |

Appearance: tan colored smooth lotion

EXAMPLE 9

|  | % |
|---|---|
| Water | 63.45 |
| Propylene Glycol | 5.00 |
| Stearyl Alcohol | 9.00 |
| Petrolatum | 5.00 |
| Oleth-20 | 5.00 |
| EDTA | 0.05 |
| Tetra Octyl Ammonium Hydroxide 40% | 12.00 |
| Fragrance | 0.50 |
|  | 100.00% |

EXAMPLE 10

|  | % |
|---|---|
| Water | 52.45 |
| Cetyl Alcohol | 9.00 |
| Paraffin | 5.00 |
| Nonoxynol-10 | 6.00 |
| Petrolatum | 5.00 |
| Mineral Oil | 5.00 |
| Glycerin | 5.00 |
| EDTA | 0.05 |
| Benzyl Dimethyl Ethanol Ammonium Hydroxide 40% | 12.00 |
| Fragrance | 0.50 |
|  | 100.00% |

The method of application of the composition of the present invention is analogous to that of the method used with conventional hair relaxers. The composition is preferably applied to clean hair so the presence of dirt or grease on hair will not inhibit or hinder the hair relaxing affect of the composition. The composition is massaged unto the hair by hand or by the use of an applicator to permeate the hair therewith. The composition is left on the hair for about ten minutes to allow for adequate softening, followed by further massaging and pressing to facilitate straightening. Subsequently, the product is rinsed off the hair and the hair is shampooed to remove all traces of the relaxer. Usually an acid rinse is also applied to neutralize any traces of the relaxer remaining in the hair.

Compositions of the present invention were tested and were found to be effective for hair relaxing.

Comparative studies were also performed. In one comparative study, 3 to 4% sodium hydroxide was used to replace the quaternary ammonium hydroxide in the cosmetic emulsion of the present invention. In another comparative study, the nonionic emulsifier of the cosmetic emulsion of the present invention was replaced by the anionic emulsifier, sodium lauryl sulfate. In both sets of studies one side of the head was treated with the composition of Example 1 while the other was treated with the composition with which the comparison was made. In the studies the subjects noted irritation within 5 minutes on the side of the head which was treated with the sodium hydroxide and the sodium lauryl sulfate containing preparations, while no irritation resulted from the composition of Example 1 for twenty minutes.

It will be understood by those skilled in the art that modifications and variations may be made without departing from the spirit and scope of the novel concept of the present invention.

What is claimed is:

1. A hair relaxer composition for straightening hair consisting essentially of by weight:
   (a) 2.0–20% of a quaternary ammonium hydroxide selected from the group consisting of benzyltrimethyl ammonium hydroxide, tetraethyl ammonium hydroxide, tetramethyl ammonium hydroxide, tetrabutyl ammonium hydroxide, tetrapropyl ammonium hydroxide, methyl triethanol ammonium hydroxide, benzyl dimethyl ethanol ammonium hydroxide, benzyltriethyl ammonium hydroxide, benzyltributyl ammonium hydroxide, octadecyl trimethyl ammonium hydroxide, tetrahexyl ammonium hydroxide, and tetraoctyl ammonium hydroxide;
   (b) 2–20% of an emulsifier selected from the group consisting of polyethylene glycol ether of cetyl alcohol, polyethylene glycol ether of lauryl alcohol, polyethylene glycol ether of nonyl phenol and polyethylene glycol ether of lanolin alcohol;
   (c) 2 to 30% of an emollient selected from the group consisting of cetyl alcohol, petrolatum, stearyl alcohol, paraffin, mineral oil, lanolin alcohol and polyethylene glycol ether of octyl phenol; and
   (d) water q.s. 100 percent.

2. A method for relaxing hair comprising the steps of:
   (a) applying to the hair by massaging unto the hair an effective amount of the hair relaxing composition of claim 1;
   (b) leaving the composition on the hair for about ten minutes to allow for adequate softening;
   (c) further massaging and pressing the hair to facilitate straightening; and
   (d) washing the hair from the hair relaxing composition.

3. The method of claim 2 wherein the composition contains methyl triethanol ammonium hydroxide.

4. The method of claim 2 wherein the composition contains tetraethyl ammonium hydroxide.

5. A hair relaxer composition for straightening hair consisting essentially of, by weight:
   (a) 2.5–20% of a quaternary ammonium hydroxide selected from the group consisting of benzyltrimethyl ammonium hydroxide, tetraethyl ammonium hydroxide, tetramethyl ammonium hydroxide, tetrabutyl ammonium hydroxide, tetrapropyl ammonium hydroxide, methyl triethanol ammonium hydroxide, benzyl dimethyl ethanol ammonium hydroxide, benzyltriethyl ammonium hydroxide, benzyltributyl ammonium hydroxide, octadecyl trimethyl ammonium hydroxide, tetrahexyl ammonium hydroxide, and tetraoctyl ammonium hydroxide;
   (b) 10–15% of an emulsifier selected from the group consisting of polyethylene glycol ether of cetyl alcohol, polyethylene glycol ether of lauryl alcohol, polyethylene glycol ether of nonyl phenol and polyethylene glycol ether of lanolin alcohol;
   (c) 5 to 25% of an emollient selected from the group consisting of cetyl alcohol, petrolatum, stearyl alcohol, paraffin, mineral oil, lanolin alcohol and polyethylene glycol ether of octyl phenol; and
   (d) water q.s. 100 percent.

6. A method for relaxing hair comprising the steps of:
   (a) applying to the hair by massaging unto the hair an effective amount of the hair relaxing composition of claim 5;
   (b) leaving the composition on the hair for about ten minutes to allow for adequate softening;
   (c) further massaging and pressing the hair to facilitate straightening; and
   (d) washing the hair from the hair relaxing composition.

7. The method of claim 6 wherein the composition contains methyl triethanol ammonium hydroxide.

8. The method of claim 6 wherein the composition contains tetraethyl ammonium hydroxide.

9. A hair relaxer composition for straightening hair consisting essentially of, by weight:
   (a) 2.5%–8.0% of a quaternary ammonium hydroxide selected from the group consisting of benzyltrimethyl ammonium hydroxide, tetraethyl ammonium hydroxide, tetramethyl ammonium hydroxide, tetrabutyl ammonium hydroxide, tetrapropyl ammonium hydroxide, methyl triethanol ammonium hydroxide, benzyl dimethyl ethanol ammonium hydroxide, benzyltriethyl ammonium hydroxide, benzyltributyl ammonium hydroxide, octadecyl trimethyl ammonium hydroxide, tetrahexyl ammonium hydroxide, and tetraoctyl ammonium hydroxide;
   (b) 10–15% of an emulsifier selected from the group consisting of polyethylene glycol ether of cetyl alcohol, polyethylene glycol ether of lauryl alcohol, polyethylene glycol ether of nonyl phenol and polyethylene glycol ether of lanolin alcohol;
   (c) 5 to 25% of an emollient selected from the group consisting of cetyl alcohol, petrolatum, stearyl alcohol, paraffin, mineral oil; lanolin alcohol or polyethylene glycol ether of octyl phenol; and
   (d) water q.s. 100 percent.

10. A method for relaxing hair comprising the steps of:

(a) applying to the hair by massaging unto the hair an effective amount of the hair relaxing composition of claim 9;
(b) leaving the composition on the hair for about ten minutes to allow for adequate softening;
(c) further massaging and pressing the hair to facilitate straightening; and
(d) washing the hair from the hair relaxing composition.

11. The method of claim 10 wherein the composition contains methyl triethanol ammonium hydroxide.

12. The method of claim 10 wherein the composition contains tetraethyl ammonium hydroxide.

* * * * *